United States Patent [19]

DeLuca et al.

[11] 4,360,472

[45] Nov. 23, 1982

[54] TRIHYDROXYVITAMIN $D_3$ COMPOUNDS

[75] Inventors: Hector F. DeLuca; Heinrich K. Schnoes; Joseph K. Wichmann, all of Madison, Wis.

[73] Assignee: Wisconsin Alumni Research Foundation, Madison, Wis.

[21] Appl. No.: 329,846

[22] Filed: Dec. 11, 1981

[51] Int. Cl.$^3$ .............................................. C07J 9/00
[52] U.S. Cl. ................................................ 260/397.2
[58] Field of Search ...................... 260/397.2; 424/236

[56] References Cited

U.S. PATENT DOCUMENTS 4,279,826  7/1981  DeLuca et al. .................. 260/397.2
4,292,249  9/1981  Nishikawa et al. ............... 260/397.2

Primary Examiner—Elbert L. Roberts
Attorney, Agent, or Firm—Howard W. Bremer

[57] ABSTRACT

A novel side chain trihydroxylated vitamin $D_3$ compound, namely 23,24,25-trihydroxyvitamin $D_3$ and its acylated and alkylsilyated derivatives are provided. The new compounds are hydroxy analogs of the biologically-active 25-hydroxyvitamin $D_3$ and would find application as substitutes for such compound or for vitamin $D_3$.

4 Claims, No Drawings

TRIHYDROXYVITAMIN D₃ COMPOUNDS

This invention relates to novel vitamin D compounds.

More specifically, this invention relates to vitamin $D_3$ derivatives bearing three hydroxy groups in the side chain.

Vitamin D is widely used therapeutically for the prevention of rickets and other bone diseases of humans, and is known to be important for the maintenance of normal blood calcium and phosphorus levels in animals and humans. It is also known that vitamin D undergoes, in vivo, a series of metabolic conversions to hydroxylated derivatives, and it is these hydroxyvitamin D metabolites which are thought to be responsible for the biological action expressed by vitamin D. Vitamin $D_3$, for example, is converted in vivo, to biologically active metabolites such as 25-hydroxyvitamin $D_3$, 1,25-dihydroxyvitamin $D_3$, 24,25-dihydroxyvitamin $D_3$ and 25,26-dihydroxyvitamin $D_3$. Vitamin $D_2$ undergoes similar metabolic conversions. The characterization of these compounds and their biological properties, as well as the preparation of related synthetic analogs, are documented in the patent and other literature.

Novel vitamin $D_3$ derivatives have now been found as represented by Formula I below. The preferred form of these derivatives is characterized by three adjacent hydroxy groups in the side chain and may be referred to as 23,24,25-trihydroxyvitamin $D_3$. The compounds are thus novel hydroxy analogs of the known and biologically-active 24,25-dihydroxyvitamin $D_3$.

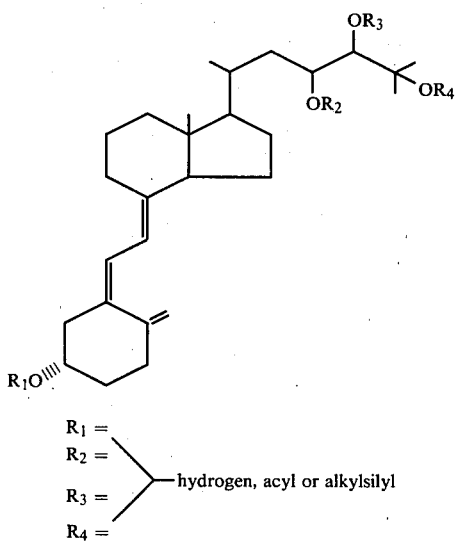

$R_1 =$
$R_2 =$
$R_3 =$  — hydrogen, acyl or alkylsilyl
$R_4 =$

The preferred trihydroxy compound was obtained in pure form by isolation from the blood of chickens which had received high doses of vitamin $D_3$.

Sixty 12-week old white Leghorn cockerels commercially available from Northern Hatcheries (Beaver Dam, WI) were raised on a commercial diet (Ralston Purina, St. Louis, MO), and each received a daily dose of $10^5$ I.U. of pure vitamin $D_3$ (dissolved in 0.05 ml of EtOH) by intramuscular injection for three days. On the fourth day, each chick received another dose of $1.5 \times 10^7$ I.U. of vitamin $D_3$ by the same route. Four days later, blood was collected from each chick by cardiac puncture. The blood was pooled, centrifuged and the resulting plasma was then extracted.

Extraction was accomplished by mixing a volume of plasma with three volumes of a 2:1 methanol/chloroform solution, and allowing the phases to separate overnight in the cold (approximately 4°–10° C.). Another volume of chloroform was then added, and the organic phase was removed. After extraction of the aqueous phase with another half volume of chloroform, the organic phases were combined and the solvent was evaporated to yield a residue which was then fractionated by chromatography.

The chloroform extract from 380 ml of plasma was chromatographed on a 3×30 cm Sephadex LH-20 column (Pharmacia, Piscataway, NJ) eluted with hexane/chloroform/methanol (9:1:1). Fractions (23 ml each) were collected and assayed for vitamin D compounds by the binding assay of Shepard et al (Biochem. J. 182, 55, 1979). The vitamin D metabolites eluting from 1150–1472 ml were collected and subjected to further purification by high-performance liquid chromatography (HPLC).

Primary HPLC purification was performed on a 0.45×25 cm microparticulate silica column (Zorbax-SIL, Dupont, Inc., Wilmington, DE) eluted with 12% 2-propanol in hexane. Standard 1,25-dihydroxyvitamin $D_3$ (1,25-$(OH)_2D_3$) eluted at about 18 ml on this system. The material eluting at about 10–12 ml was collected for the further purification of the desired metabolite. These fractions were then subjected to HPLC on a 0.45×25 cm reverse phase column (silica-bonded octadecylsilane, Zorbax-ODS; Dupont, Inc., Wilmington, DE) eluted with 20% water in methanol. Standard 1,25-$(OH)_2D_3$ eluted at 25 ml on this system. The desired metabolite was eluted at 7–8 ml.

Final purification of the trihydroxy compound was performed on a 0.45×25 cm microparticulate silica column eluted with 14% 2-propanol in hexane. The compound eluted at 7.5–9.5 ml.

This sequence of steps provided the desired compound in pure form. The compound exhibited an ultraviolet absorption maximum at $\lambda_{max}=265$ nm.

The structure of the recovered compound was established by spectroscopy as follows:

The ultraviolet absorption of the trihydroxy compound at 265 nm indicated an intact vitamin D 5,6-cis-triene chromophore and its chromatographic polarity suggested the incorporation of three additional hydroxy groups. To determine the number of the hydroxy groups and their location, the compound was converted to its trimethylsilyl (TMS) ether derivative by treatment with N,O-bis-trimethylsilyltrifluoroacetamide containing 1% trimethylsilyl chloride in pyridine at 30°–50° C., and the resulting product was subjected to mass spectrometric analysis. The mass spectrum showed a molecular ion at m/e 720 as expected for the tetra-trimethylsilyl ether product of a trihydroxyvitamin $D_3$ derivative. The presence of peaks at m/e 208 and 118 (208-HOTMS), which are characteristic ring-A fragments of vitamin $D_3$-O-TMS ether, confirmed the presence of the C-3-hydroxy group and the fact that the typical vitamin $D_3$-ring A and triene system were unaltered. The position of the three additional hydroxy groups in the side chain was apparent from prominent peaks at m/e 131 and 487. The peak at m/e 131 results from cleavage between C24 and C25 and represents the ion $[(CH_3)_2C=O-Si(CH_3)_3]^+$ comprising carbons 25, 26 and 27 of the side chain. This peak is characteristic for 25-O-TMS derivatives and thus establishes the presence of a hydroxy group at carbon 25, and also the absence of any hydroxy substitution at carbon 26 or 27. The peak at m/e 487 (as well as the peaks at m/e 397 and 307, which result from successive elimination of HOTMS from 487), arises by cleavage of the C-23,24 bond and requires the presence of a C-23-OTMS substituent and the absence of any hydroxy substitution at carbons 22, 21 or 20. Thus, two of the hydroxy groups are positively localized carbons 23 and 25, and since all other positions are excluded, the third must then be assigned to carbon 24.

These data, therefore, establish the structure of the trihydroxy compound as 23,24,25-trihydroxyvitamin $D_3$.

23,24,25-trihydroxyvitamin $D_3$ can be readily converted to other useful derivatives, e.g. acyl or alkylsilyl derivatives, by treatment with appropriate acylating or alkylsilylating reagents under standard conditions. Suitable acylating reagents are acyl chlorides or acid anhydrides, and suitable alkylsilylating reagents are alkylsilylhalides or analogous activated alkylsilyl derivatives. Thus, for example, treatment with acetic anhydride at a temperature of 25°–50° C. in pyridine yields the 3,23,24-triacetyl derivatives, whereas the reaction conducted at elevated temperatures (75°–100° C.) yields the tetracetyl product. Other desirable acylderivatives such as the propionyl, butyryl, trihaloacetyl, benzoyl, nitro- and halo-benzoyl derivatives, can be obtained via the appropriate acid anhydride or acylhalide by analogous procedures. Partially acylated derivatives can then be further acylated by a different acyl group or can by alkylsilylated by treatment with alkylsilylhalide reagents, wherein the alkyl group represents a hydrocarbon radical of from 1 to about 5 carbons, e.g. methyl, ethyl, propyl, butyl, tert.-butyl, etc.

As will be evident from formulae I the trihydroxy compound of this invention is an analog of 24,25-dihydroxyvitamin $D_3$, a vitamin D metabolite of established biological potency. It would be expected, therefore, that this trihydroxy compound is characterized by in vivo vitamin D-like activity and, therefore, could be utilized as a substitute for vitamin $D_3$ or other side chain-hydroxylated vitamin D metabolites in their known therapeutic and other applications.

Having thus described the invention, what is claimed is:

1. A compound having the formula:

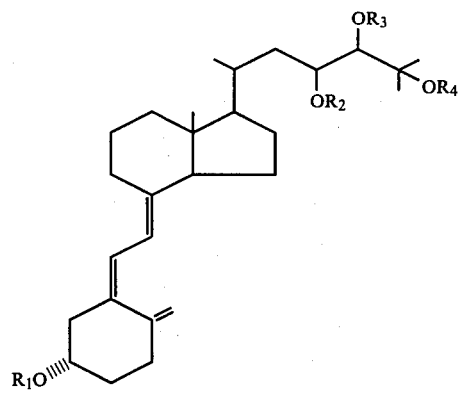

wherein each of $R_1$, $R_2$, $R_3$ and $R_4$ is selected from the group consisting of hydrogen, acyl and alkylsilyl.

2. The compound of claim 1 wherein each of $R_1$, $R_2$, $R_3$ and $R_4$ is acetyl or benzoyl.

3. 23,24,25-trihydroxyvitamin $D_3$.

4. The compound of claim 3 in crystalline form.